(12) United States Patent
Harris et al.

(10) Patent No.: US 10,881,591 B2
(45) Date of Patent: Jan. 5, 2021

(54) INTEGRAL POROUS FIBER MEDIA WITH DISTINGUISHABLE DENSITY OR FIBER DIAMETERS

(71) Applicant: POREX TECHNOLOGIES CORPORATION, Colonial Heights, VA (US)

(72) Inventors: David Harris, Midlothian, VA (US); Yelena Rogova, Richmond, VA (US); Qiang Zhou, Moseley, VA (US); Guoqiang Mao, Smyrna, GA (US)

(73) Assignee: POREX TECHNOLOGIES CORPORATION, Colonial Heights, VA (US)

( * ) Notice: Subject to any disclaimer, the term of this patent is extended or adjusted under 35 U.S.C. 154(b) by 0 days.

(21) Appl. No.: 15/994,834

(22) Filed: May 31, 2018

(65) Prior Publication Data
US 2018/0360697 A1    Dec. 20, 2018

Related U.S. Application Data

(60) Provisional application No. 62/581,302, filed on Nov. 3, 2017, provisional application No. 62/520,352, filed on Jun. 15, 2017.

(51) Int. Cl.
*A45D 37/00*    (2006.01)
*A61L 15/00*    (2006.01)
(Continued)

(52) U.S. Cl.
CPC ............. *A61K 8/027* (2013.01); *A45D 37/00* (2013.01); *A61K 8/0279* (2013.01); *A61K 8/87* (2013.01);
(Continued)

(58) Field of Classification Search
CPC .... A45D 2200/1018; A45D 2200/1036; A45D 37/00; A61K 8/027; A61K 8/0279; A61K 8/87; A61L 15/00
See application file for complete search history.

(56) References Cited

U.S. PATENT DOCUMENTS

| 4,032,688 A | 6/1977 | Pall |
| 5,403,482 A | 4/1995 | Steere et al. |

(Continued)

FOREIGN PATENT DOCUMENTS

| CN | 106133226 A | 11/2016 |
| DE | 6940428 T2 | 2/1998 |

(Continued)

OTHER PUBLICATIONS

Du et al. (Fibers and Polymers 2008;9(1):27-33) (Year: 2008).*

(Continued)

*Primary Examiner* — Ernst V Arnold
(74) *Attorney, Agent, or Firm* — Troutman Pepper Hamilton Sanders LLP

(57) ABSTRACT

The instant disclosure relates to an integral porous fiber media with distinguishable distribution of fiber density, fiber diameter and capillary force. The instant disclosure further relates to a fiber porous media that includes multiple density portions. The disclosed media is a single piece, such that the different density portions are not separable. The disclosed media provides improved liquid delivery properties for a specific liquid delivery device.

14 Claims, 11 Drawing Sheets

(51) Int. Cl.
    *A61K 8/02*     (2006.01)
    *A61K 8/87*     (2006.01)

(52) U.S. Cl.
    CPC ............... *A45D 2200/1018* (2013.01); *A45D 2200/1036* (2013.01)

(56) References Cited

U.S. PATENT DOCUMENTS

| | | |
|---|---|---|
| 5,562,825 A | 10/1996 | Yamada et al. |
| 5,607,766 A | 3/1997 | Berger |
| 5,620,641 A | 4/1997 | Berger |
| 5,633,082 A | 5/1997 | Berger |
| 5,643,507 A | 7/1997 | Berrigan et al. |
| 5,672,399 A | 9/1997 | Kahlbaugh et al. |
| 6,103,181 A | 8/2000 | Berger |
| 6,169,045 B1 * | 1/2001 | Pike ............... B01D 39/163 442/352 |
| 6,273,938 B1 | 8/2001 | Fanselow et al. |
| 6,330,883 B1 | 12/2001 | Berger |
| 6,840,692 B2 | 1/2005 | Ward et al. |
| 7,018,031 B2 | 3/2006 | Ward et al. |
| 7,888,275 B2 | 2/2011 | Ward et al. |
| 8,939,295 B2 | 1/2015 | Ward et al. |
| 9,585,456 B2 | 3/2017 | Choi et al. |
| 2003/0226339 A1 | 12/2003 | Igarashi |
| 2004/0023689 A1 | 1/2004 | Kim et al. |
| 2004/0060269 A1 | 4/2004 | Chung et al. |
| 2010/0181249 A1 | 7/2010 | Green et al. |
| 2010/0206803 A1 | 8/2010 | Ward et al. |
| 2011/0070423 A1 | 3/2011 | Jayakody et al. |
| 2011/0290716 A1 | 12/2011 | Tada et al. |
| 2011/0318244 A1 | 12/2011 | Ausner et al. |
| 2012/0107387 A1 | 5/2012 | Ochiai et al. |
| 2013/0012689 A1 * | 1/2013 | Singh ............... B01D 15/3809 530/388.1 |
| 2013/0014883 A1 | 1/2013 | Hartmann et al. |
| 2013/0206683 A1 | 8/2013 | Behrendt et al. |
| 2015/0231531 A1 | 8/2015 | Dillie et al. |
| 2015/0290562 A1 | 10/2015 | Oberli et al. |
| 2018/0023215 A1 | 1/2018 | Robertson et al. |

FOREIGN PATENT DOCUMENTS

| | | |
|---|---|---|
| WO | 2015127120 A1 | 8/2015 |
| WO | 2017016608 A1 | 2/2017 |
| WO | 2018231537 A1 | 12/2018 |

OTHER PUBLICATIONS

Fiber Measurement Conversions [online] retrieved on Aug. 19, 2020 from: https://www.minifibers.com/our-connpany/about-fibers/fiber-measurement-conversions/; page (Year: 2020).*

International Search Report and Written Opinion for PCT/US2015/016680 dated Jun. 29, 2015.

International Search Report and Written Opinion for PCT/US2018/035445 dated Aug. 24, 2018.

* cited by examiner

INTEGRAL POROUS FIBER MEDIA WITH DISTINGUISHABLE DENSITY OR FIBER DIAMETERS

CROSS-REFERENCE TO RELATED APPLICATIONS

This application claims benefit of and priority to U.S. Provisional Patent Application No. 62/520,352 entitled "Media Reservoir Having a Capillarity Gradient," filed Jun. 15, 2017, the disclosure of which is incorporated by reference herein in its entirety. This application further claims benefit of and priority to U.S. Provisional Patent Application No. 62/581,302 entitled "Integral Porous Fiber Media with Distinguishable Density or Fiber Diameters for Cosmetic Holding Media and Application of the Same," filed Nov. 3, 2017, the disclosure of which is incorporated by reference herein in its entirety.

FIELD OF THE INVENTION

The present disclosure is related to an integral porous fiber media with distinguishable distribution of fiber density, fiber diameter and capillary force for depository and delivery of a fluid.

BACKGROUND

There are several techniques for delivering a media from a reservoir. For example, a mechanical device such as a brush, direct applicator, foam, pad, or other similar device can be absorb a portion of or otherwise direct fluid from the reservoir to a point where the fluid can be used. Such an applicant means is typically used, for example, in cosmetic applications, ink jet printing, and other similar applications.

U.S. Patent Application Publication No. 2014/0023689, the content of which is incorporated herein by reference in its entirety, discloses a cushion compact format cosmetic product using urethane foam impregnated with a cosmetic composition. However, urethane based polymer foam has chemical compatibility issues with some cosmetic ingredients and, as such, cannot be used for all cosmetic ingredients. Also, urethane based polymer foam does not provide desirable release performance, resulting in a large amount of waste of cosmetic formula.

U.S. Pat. No. 9,585,456, the content of which is incorporated herein by reference in its entirety, discloses a cushion compact format cosmetic product using open cell foam impregnated with cosmetic composition. However, open cell foam lacks a smooth and appealing surface feature and has chemical compatibility issues with some cosmetic ingredients in long-term usage.

International Patent Application Publication WO2017016608, the content of which is incorporated herein by reference in its entirety, discloses a cushion compact format cosmetic product using a screen on top of non-woven fiber media. Although the screen provides an improved appearance for the cushion, the screen is easy separated from the underneath nonwoven media and results in poor performance and consumer experience. If the screen is permanently attached to the non-woven media, the resulted cushion cannot be flipped over when needed.

In other examples, fluid reservoirs, such as fiber reservoirs, are used in most ink cartridges for ink jet printers. The reservoirs help to regulate the flow of ink from a free ink reservoir to a wick at an outlet port. Reservoirs help to ensure consistent ink flow from the free ink reservoir to the outlet port, and help to prevent ink leakage from the ink cartridge. Current ink cartridges typically employ an ink absorbing material made from a block of porous material or foam in the reservoir. These materials provide a capillary effect to hold ink and prevent leakage. However, at the end of the life cycle of the ink cartridge, ink is retained in the absorbing material. This remaining ink is then discarded with the spent cartridge, wasting otherwise usable ink.

Markets need an improved porous fiber media that provide improved efficiency in delivering, for example, a fluid from a reservoir for use in various applications.

SUMMARY

There is described an integral porous fiber matrix. In some embodiments, the matrix includes at least one of a plurality of density regions, wherein each of the plurality of density regions has a different fiber density, and a plurality of diameter regions, wherein each of the plurality of diameter regions has a different fiber diameter.

In some embodiments, each of the density regions includes a unique layer.

In some embodiments, each of the plurality of diameter regions includes a unique layer.

In some embodiments, the matrix is integrated into a cushioned disk configured to hold and release a quantity of one or more cosmetic compositions.

In some embodiments, the matrix further includes bicomponent fibers.

There is also disclosed an integral porous fluid depository and delivery media including an integral porous fiber matrix. In some embodiments, the matrix includes at least one of a plurality of density regions, wherein each of the plurality of density regions has a different fiber density, and a plurality of diameter regions, wherein each of the plurality of diameter regions has a different fiber diameter.

In some embodiments, each of the density regions includes a unique layer.

In some embodiments, a change in density of the plurality of density regions is gradual.

In some embodiments, each of the plurality of diameter regions includes a unique layer.

In some embodiments, the matrix is integrated into a cushioned disk configured to hold and release a quantity of one or more liquid compositions.

In some embodiments, the matrix further includes bicomponent fibers. In some additional embodiments, the bicomponent fiber include at least one of polypropylene/polyethylene terephthalate (PET), polyethylene (PE)/PET, polyethylene/polypropylene, polypropylene/Nylon-6, Nylon-6/PET, copolyester/PET, copolyester/Nylon-6, copolyester/Nylon-6,6, poly-4-methyl-1-pentene/PET, poly-4-methyl-1-pentene/Nylon-6, poly-4-methyl-1-pentene/Nylon-6,6, PET/polyethylene naphthalate (PEN), Nylon-6,6/poly-1,4-cyclohexanedimethy-1 (PCT), polypropylene/polybutylene terephthalate (PBT), Nylon-6/co-polyamide, polyester/polyester and polyurethane/acetal.

In some embodiments, the fluid includes at least one of a writing instrument ink, an inkjet ink, a cosmetic composition, a foundation, a perfume, a sunscreen, an oil, a gel, and a liquid therapeutic agent.

In some embodiments, the fiber density includes a varying range including at least one of 0.005 $g/cm^3$ to 0.2 $g/cm^3$, from 0.01 $g/cm^3$ to 0.18 $g/cm^3$, and from 0.02 $g/cm^3$ to 0.15 $g/cm^3$.

In some embodiments, the fiber diameter includes a varying range including at least one of 1 dtex to 20 dtex, from 2 dtex to 15 dtex, and from 3 dtex to 10 dtex.

In some embodiments, different density regions include different capillary forces.

In some embodiments, gradient density regions include gradient capillary forces.

There is also disclosed a fluid application device including at least one integral porous fluid depository and a delivery media including an integral porous fiber matrix. In some embodiments, the matrix includes at least one of a plurality of density regions, wherein each of the plurality of density regions has a different fiber density, and a plurality of diameter regions, wherein each of the plurality of diameter regions has a different fiber diameter.

In some embodiments, the device includes at least one of a cushion compact foundation device, a perfume application device, a makeup device, an ink jet printer cartridge, a writing instrument, and a medical device.

DETAILED DESCRIPTION

Figure 1A:
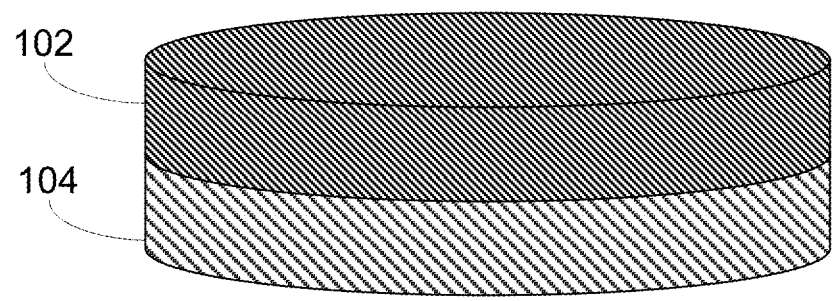
FIGS. 1A-1J illustrate various arrangements of fiber media in accordance with one or more embodiments described herein.

This disclosure is not limited to the particular systems, devices, and methods described, as these may vary. The terminology used in the description is for the purpose of describing the particular versions or embodiments only, and is not intended to limit the scope of the disclosure.

The following terms shall have, for the purposes of this application, the respective meanings set forth below. Unless otherwise defined, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used herein, the singular forms "a," "an," and "the" include plural references, unless the context clearly dictates otherwise. Thus, for example, reference to a "fiber" is a reference to one or more fibers and equivalents thereof known to those skilled in the art, and so forth.

As used herein, the term "fluid: includes a substance that has no fixed shape and yields to external pressure. For example, fluids can include gases and liquids. As used herein, the term fluid or liquid may be used interchangeable and, for the purposes of this disclosure, include a substance having a flow directed by a particular media including, for example, an integral porous fiber media as described herein. Examples of fluids as described herein can include writing instrument inks, inkjet inks, cosmetic compositions, foundations, perfumes, sunscreens, oils, gels, liquid therapeutic agents, and other similar liquids and fluids.

In certain implementations, the present disclosure is about an integral porous fiber media with distinguishable distribution of fiber density, fiber diameter and capillary force. As used herein, integral means that different distinguishable regions are formed together during manufactural process and they could not be separated without damaging an individual region. In certain implementations, the distinguishable regions can be distributed in a layered structure.

In a sample embodiment, the integral porous fiber media can be in a disk form and the disks have distinguishable distribution of a fiber matrix's density or void volume cross the disk's thickness.

In another sample embodiment, the integral porous fiber media can be in a disk form and the disks have distinguishable distribution of fiber diameters cross the disk's thickness.

In another sample embodiment, the integral porous fiber media can be in a disk form and the disks have distinguishable distribution of fiber matrix's density and fiber diameters cross the disk's thickness.

In some examples, the fibers of integral porous fiber media are bonded together at the spaced spots by heat. In certain implementations, the integral porous fiber media is hydrophilic.

In certain other implementations, the present disclosure relates to a single-piece liquid depository and dispensing media. As noted above, in traditional designs, a fiber reservoir can be made from a block of porous material or foam. In certain designs, materials having varying capillary forces can be positioned adjacent to each other to provide varying levels of density. However, these materials are positioned adjacent to one another, thereby resulting in a defined interface between the different materials.

The single-piece liquid depository and dispensing media as taught herein includes, for example, a fluid reservoir configured to hold a quantity of fluid. In certain implementations, the fluid can include ink (such as ink-jet printer ink), cosmetics fluid, pharmaceuticals, analytic solutions, and other similar fluids. The fluid reservoir can also include a fiber porous matrix that is configured such that the matrix includes variances in density or open spaces, fiber diameter, and/or surface tension. By including the variances in these aspects of the fiber matrix, differences in capillary forces for different regions of the fiber matrix can be achieved. Additionally, the differences in capillary forces can be arranged such that they vary from top to bottom of the fiber matrix, as well as from side to side. Such a design, including a single-piece fluid holding reservoir with a capillary gradient as described herein, can provide for a higher level of total fluid release during normal use as compared to conventional capillary techniques that use an interface between fluid release materials as described above.

Additionally, in various implementations, the media as described herein can be integrated in various devices. For example, the media can be integrated into cushion compact foundation devices, perfume application devices, makeup devices, ink jet printer cartridges, writing instruments, medical devices, and other similar fluid or liquid delivery devices.

Integral Porous Fiber Disks

As noted above, the present disclosure teaches an integral porous fiber media. In one example as illustrated in FIG. 1A, the integral porous fiber disks can have a higher density at one surface than another surface. For example, as shown in FIG. 1A, integral porous fiber disk 100 can include an upper surface having a higher density porous fiber layer 102 and a lower surface having a lower density porous fiber layer 104.

Figure 1B:
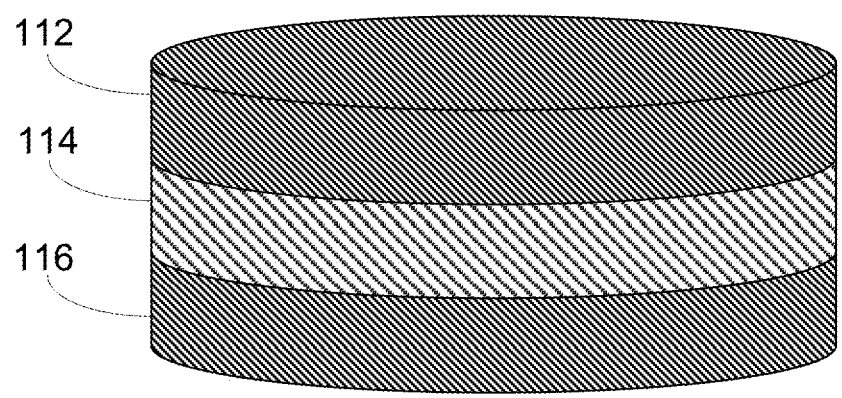

In another example as illustrated in FIG. 1B, an integral porous fiber disk can have a higher density at both surfaces than the density in the middle. For example, as shown in FIG. 1B, an integral porous fiber disk 110 can include a lower density porous fiber layer 114 that is sandwiched between two higher density porous fiber layers 112 and 116.

Figure 1C:
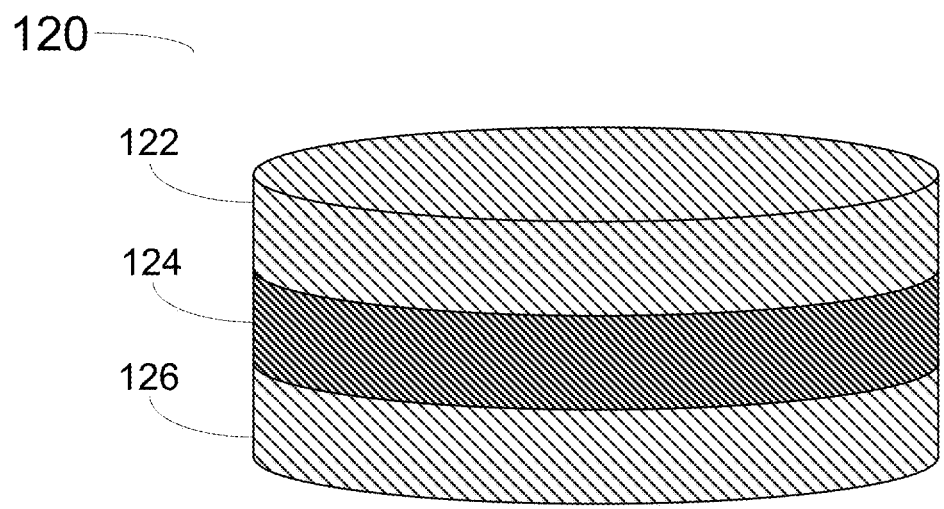

In another example as illustrated in FIG. 1C, an integral porous fiber disk can have a lower density at both surfaces than the density in the middle. For example, as shown in FIG. 1C, an integral porous fiber disk 120 can include a higher density porous fiber layer 124 that is be sandwiched between two lower density porous fiber layers 122 and 126.

Figure 1D:
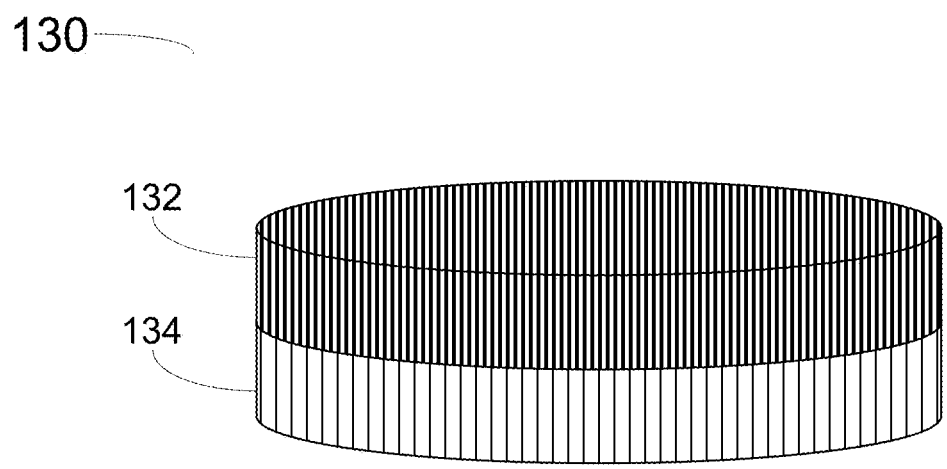

As noted above, in addition to varying fiber density, the fiber disks can include layers with varying fiber diameters. In one example as illustrated in FIG. 1D, the fibers at one surface of an integral porous fiber disks have the smaller diameter than the fibers in other part of disk. For example, as shown in FIG. 1D, an integral porous fiber disk 130 can include an upper surface having a fiber layer 132 with small diameter fibers and a lower surface having a fiber layer 134 with large diameter fibers.

Figure 1E:
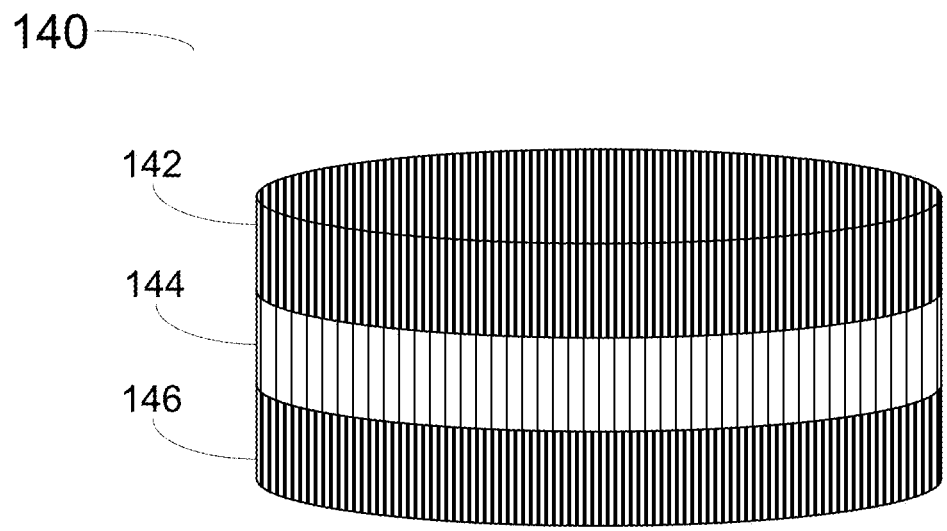

In another example as illustrated in FIG. 1E, the fibers at both surfaces of integral porous fiber disks can have smaller diameter as compared to the fibers in the middle of disk. For example, as shown in FIG. 1E, an integral porous fiber disk 140 can include a large diameter fiber layer 144 that is sandwiched between two small diameter fiber layers 142 and 146.

Figure 1F:
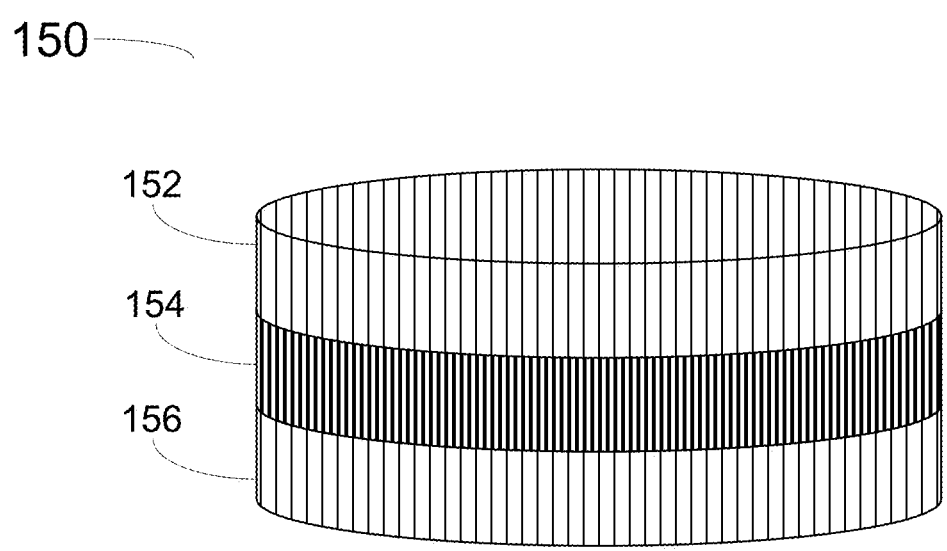

In another example as illustrated in FIG. 1F, the fibers at both surfaces of integral porous fiber disks can have larger diameter as compared to the fibers in the middle of disk. For example, as shown in FIG. 1F, an integral porous fiber disk 150 can include a smaller diameter fiber layer 154 that is sandwiched between two large diameter fiber layers 152 and 156.

Figure 1G:
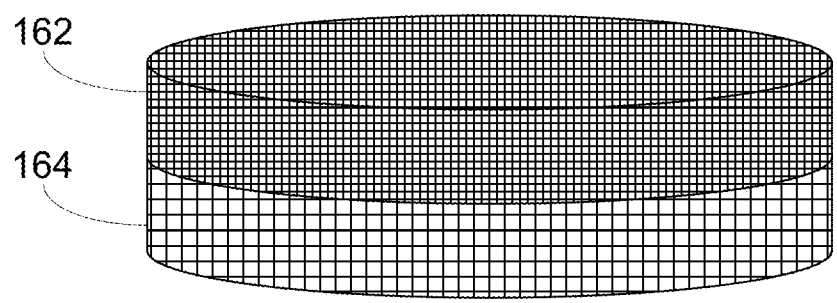

The media layers can also include a combination of varying densities and fiber diameters. In one example as illustrated in FIG. 1G, the fibers at one surface of integral porous fiber disks can have a smaller diameter than fibers in other parts of the disk and fiber matrix formed by the smaller diameter fibers has a higher density than the other part of disk. For example, as shown in FIG. 1G, an integral porous fiber disk 160 can include an upper layer 162 that is a porous fiber layer with smaller diameter fibers and a higher fiber density, and a lower layer 164 that is a porous fiber layer with larger diameter fibers and a lower fiber density.

Figure 1H:
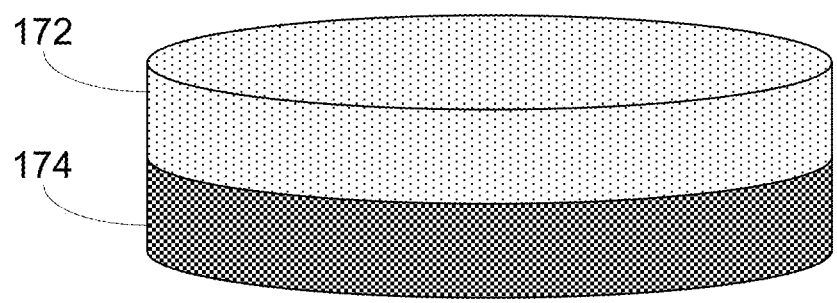

In another example as illustrated in FIG. 1H, the fibers at one surface of integral porous fiber disks can have a smaller diameter than fibers in other parts of the disk and fiber matrix formed by the smaller diameter fibers has a lower density than the other part of disk. For example, as shown in FIG. 1H, an integral porous fiber disk 170 can include an upper layer 172 that is a porous fiber layer with smaller diameter fibers and a lower fiber density, and a lower layer 174 that is a porous fiber layer with larger diameter fibers and a higher fiber density.

Figure 1I:
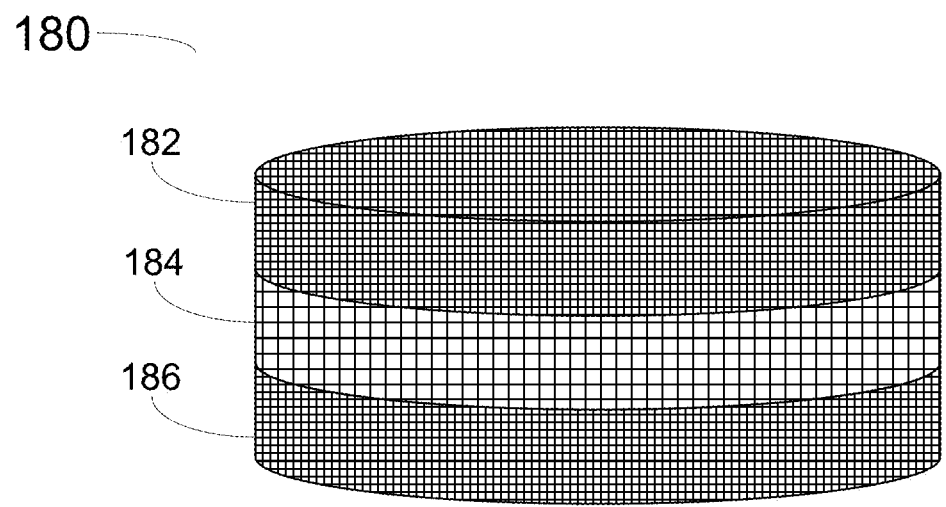

In another example as illustrated in FIG. 1I, the fibers at both surfaces of an integral porous fiber disk can have a smaller diameter than the fibers in middle of disk, and fiber matrix formed by smaller diameter fiber at both surface have a higher density than the middle part of disk. For example, as shown in FIG. 1I, an integral porous fiber disk 180 can include a porous fiber layer 184 with larger diameter fibers and a lower fiber density that is sandwiched between porous fiber layers 182 and 186, each having smaller diameter fibers and higher fiber density as compared to layer 184.

Figure 1J:
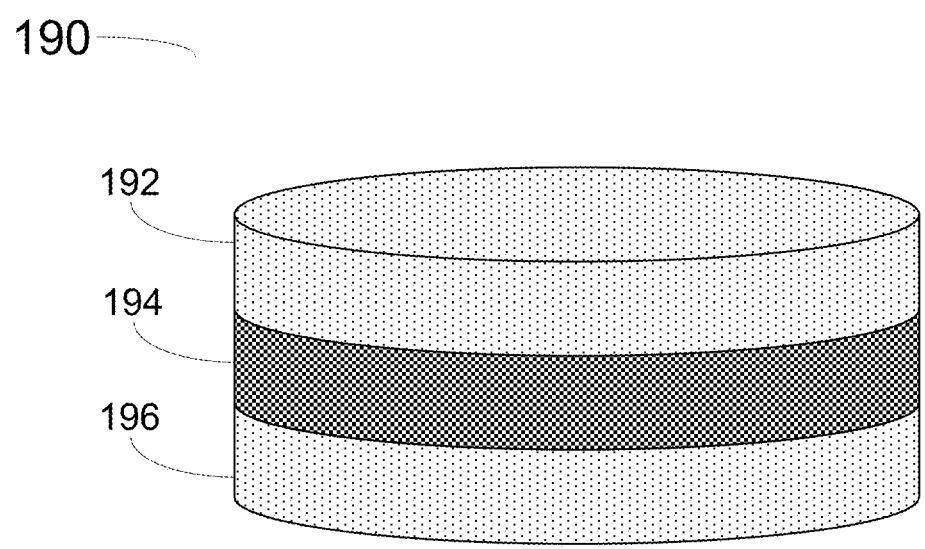

In another example as illustrated in FIG. 1J, the fibers at both surfaces of integral porous fiber disk can have a smaller diameter than the fibers in middle of disk, and fiber matrix formed by smaller diameter fiber at both surface have a lower density than the density of middle part of disk. For example, as shown in FIG. 1J, an integral porous fiber disk 190 can include a porous fiber layer 194 with larger diameter fibers and a higher fiber density that is sandwiched between porous fiber layers 192 and 196, each having smaller diameter fibers and lower fiber density.

In certain implementations, the integral porous fiber disks can include a plurality of layers. A plurality of layers can include a two layer structure, a three layers structure, or more than three layers structures.

In other implementations, the integral porous fiber disks can have a density gradient structure. For example, a density gradient can include the fiber matrix density gradually changing from one surface to another surface or from the surfaces of the disk to the middle of the disk. There is no clear boundary between the high density and low density regions.

In some examples, the plurality of fiber layers of the porous fiber disks can include individual layers of carded non-woven webs. In other embodiments, the individual layers include a woven material. In another embodiment, the individual layers include a staple fiber. In another embodiment, the individual layers include a continuous fiber. In other embodiments, the fibers of the individual layers have a fiber mass in the range of from about 1 to about 20 dtex.

In some examples related to cosmetic liquid depository and dispensing applications, the high density layer may have a density ranging from about 0.03 g/cm$^3$ to about 0.2 g/cm$^3$. In another embodiment, the high density fiber layer may have a density ranging from about 0.04 g/cm$^3$ to about 0.18 g/cm$^3$. In another embodiment, the high density fiber layer may have a density ranging from about 0.05 g/cm$^3$ to about 0.16 g/cm$^3$. In yet another embodiment, the high density fiber layer may have a density ranging from about 0.06 g/cm$^3$ to about 0.15 g/cm$^3$. In some embodiments, the high density fiber layer may have a density ranging from about 0.07 g/cm$^3$ to about 0.14 g/cm$^3$. In some embodiments, the high density fiber layer may have a density ranging from about 0.08 g/cm$^3$ to about 0.13 g/cm$^3$. In some embodiments, the high density fiber layer may have a density ranging from about 0.09 g/cm$^3$ to about 0.12 g/cm$^3$. In one embodiment, the density of the smaller diameter fiber layer has a greater density than the large diameter fiber layer. In one embodiment, the low density fiber layer may have a density ranging from about 0.005 g/cm$^3$ to about 0.10 g/cm$^3$. In one embodiment, the low density fiber layer may have a density ranging from about 0.008 g/cm$^3$ to about 0.09 g/cm$^3$. In one embodiment, the low density fiber layer may have a density ranging from about 0.01 g/cm$^3$ to about 0.08 g/cm$^3$. In one embodiment, the low density fiber layer may have a density ranging from about 0.02 g/cm$^3$ to about 0.07 g/cm$^3$. In one embodiment, the low density fiber layer may have a density ranging from about 0.03 g/cm$^3$ to about 0.06 g/cm$^3$.

In a specific example, the high density layer and low density layer are relative. In an integral porous fiber part, the ratio of the density of high density layer to the density of low density layer may be 1.1 to 1, 1.2 to 1, 1.3 to 1, 1.4 to 1, 1.5 to 1, 1.6 to 1, 1.7 to 1, 1.8 to 1, 1.9 to 1, 2.0 to 1, 2.2 to 1, 2.4 to 1, 2.6 to 1, 2.8 to 1 or 3.0 to 1.

In at least one embodiment, the small diameter fibers may have a diameter ranging from about 1 dtex to about 6 dtex. In another embodiment, the small diameter fibers may have a diameter ranging from about 2 dtex to about 5 dtex. In another embodiment, the small diameter fibers may have a diameter ranging from about 3 dtex to about 4 dtex. In one embodiment, the density of the small diameter fiber layer is greater than the density of the large diameter fiber layer. In one embodiment, the large diameter fibers may have a diameter ranging from about 4 dtex to about 20 dtex. In another embodiment, the large diameter fibers may have a diameter ranging from about 6 dtex to about 16 dtex. In another embodiment, the large diameter fibers may have a diameter ranging from about 8 dtex to about 12 dtex.

In one embodiment, the porous fiber matrix includes bicomponent fibers. In another embodiment, the porous fiber matrix includes bicomponent fibers and mono-component fibers.

In some embodiments, the fibers can include one or more of a polyester and a co-polyester. In certain embodiments, the polyester or co-polyester can include one or more of polyethylene terephthalate (PET), polybutylene terephthalate (PBT), polytrimethylene terephthalate (PTT) and poly (lactic acid) (PLA). In one embodiment, the fiber layers may include fibers made from PLA. Bicomponent fibers that may be employed in the practice of this invention include, but are not limited to fibers constructed from the following pairs of polymers: polypropylene/polyethylene terephthalate (PET), polyethylene (PE)/PET, polyethylene/polypropylene, polypropylene/Nylon-6, Nylon-6/PET, copolyester/PET, copolyester/Nylon-6, copolyester/Nylon-6,6, poly-4-methyl-1-pentene/PET, poly-4-methyl-1-pentene/Nylon-6, poly-4-methyl-1-pentene/Nylon-6,6, PET/polyethylene naphthalate (PEN), Nylon-6,6/poly-1,4-cyclohexanedimethy-1 (PCT), polypropylene/polybutylene terephthalate (PBT), Nylon-6/co-polyamide, polyester/polyester and polyurethane/acetal.

The integral porous fiber media in present invention can have a void volume at least of 60%, at least of 70%, at least of 80%, at lease of 90%, at least of 91%, at least of 92%, at least of 93%, at least of 94%, or at least of 95%.

Cosmetic composition for foundations as described herein can be liquids with a viscosity range from about 500 cps to about 50,000 cps, from 1000 cps to about 40,000 cps, or from 5000 to 20,000 cps. One specific cosmetic composition can include sun protection factor (SPF) from 15 to above 50.

A comparison with a commercially available open cell based cushion compact cushion with a cushion including a two layer porous fiber cushion according to the techniques as described herein. The basic properties for the new cushion are listed in TABLE 1:

TABLE 1

| Sample | Fiber direction | Fiber diameter (dtex) | Thickness (mm) | Diameter (mm) | Density over all g/cc | Density 4 Dtex layer g/cc | Density 8 Dtex layer g/cc |
|---|---|---|---|---|---|---|---|
| New Design | Horizontal | 4 top and 8 bottom | 12.2 | 48.2 | 0.042 | 0.055 | 0.040 |

However, it should be noted that the cushion as described in TABLE 1 is provided by way of example only. In certain implementations, various numbers of layers other than two or three as described herein can be used. For example, a cushion can include a seven layer arrangement including different fiber diameters on each layer. TABLE 2 below shows a sample set of detail about a cushion compact disk with a seven layer configuration, each configuration A and B having finer or smaller diameter fibers on the external surface:

TABLE 2

| Sample | Fiber diameter distribution | Weight, g | Diameter, mm | Thickness, mm | Density, g/cc |
|---|---|---|---|---|---|
| A | 4-8-8-8-8-8-4 | | | | |
| 1 | | 1.2267 | 49.73 | 11.31 | 0.056 |
| 2 | | 1.1931 | 49.75 | 11.40 | 0.054 |
| 3 | | 1.1818 | 49.75 | 11.38 | 0.053 |
| Avg | | 1.2005 | 49.74 | 11.36 | 0.054 |
| SD | | 0.023 | 0.012 | 0.047 | 0.001 |
| B | 4-4-8-8-8-4-4 | | | | |
| 1 | | 1.1157 | 49.77 | 11.89 | 0.048 |
| 2 | | 1.1586 | 49.81 | 11.42 | 0.052 |
| 3 | | 1.1799 | 49.74 | 11.77 | 0.052 |
| Avg | | 1.1514 | 49.77 | 11.69 | 0.051 |
| SD | | 0.033 | 0.035 | 0.244 | 0.002 |

TABLE 3 below shows specific details about the above-identified samples appearance and recovery after a compression test:

TABLE 3

| Sample | Top layer | Diameter, mm | Thick., mm | Void volume, cc | Density, g/cc | *Instant Recovery, % | *24 hours Recovery, % |
|---|---|---|---|---|---|---|---|
| A | Fine thin | 49.5 | 11.0 | 20.0 | 0.050 | 97 | 99 |

TABLE 3-continued

| Sample | Top layer | Diameter, mm | Thick., mm | Void volume, cc | Density, g/cc | *Instant Recovery, % | *24 hours Recovery, % |
|---|---|---|---|---|---|---|---|
| B | Fine thick | 49.5 | 11.0 | 20.0 | 0.050 | 97 | 100 |

Single-Piece Media Dispensing Device

Figure 2:
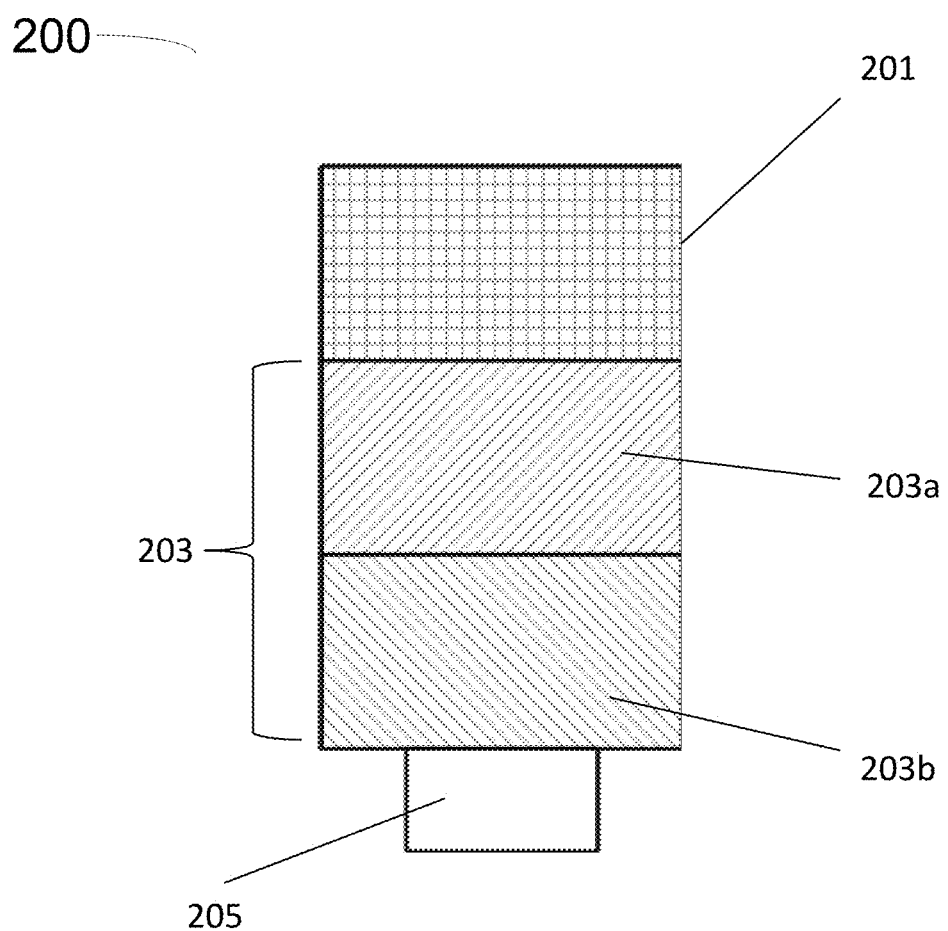
FIG. 2 illustrates a media dispensing device in accordance with one or more embodiments described herein.
Figure 3:
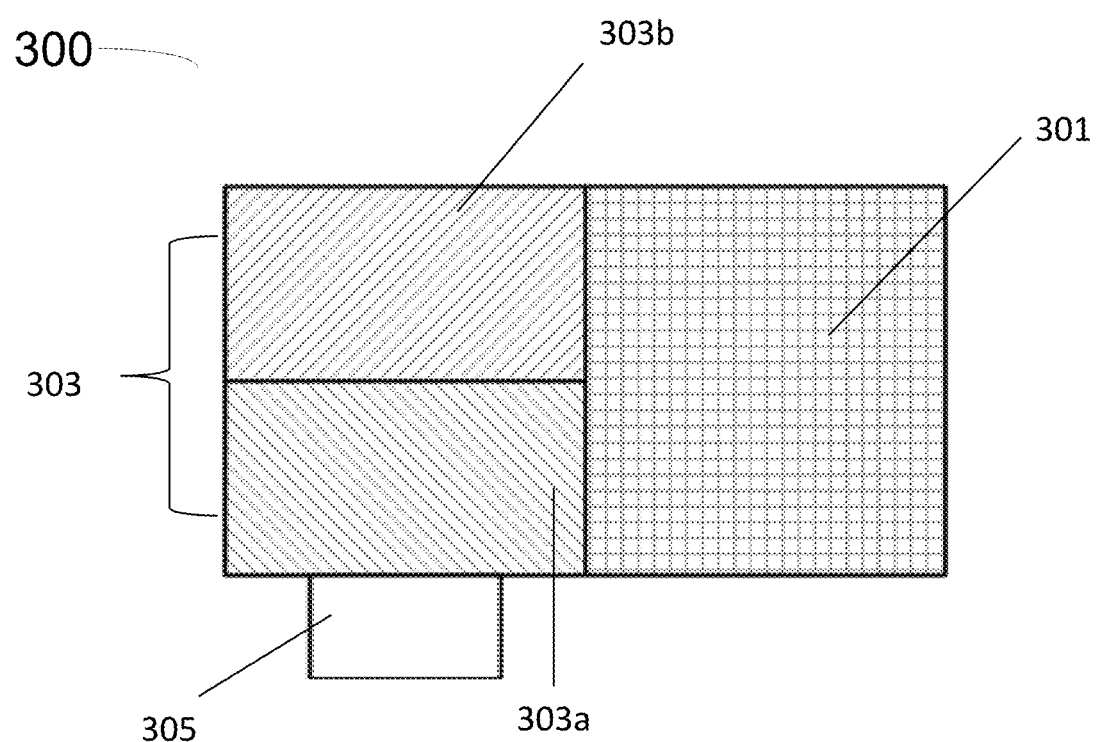
FIG. 3 illustrates an alternative media dispensing device in accordance with one or more embodiments described herein.

FIG. 2 illustrates a sample single-piece liquid depository and dispensing media 200. In FIG. 1, the media dispensing device 200 includes a fluid reservoir 201 and a gradient density reservoir 203 in fluid communication with the fluid reservoir 200. The gradient density reservoir 203 includes two portions or sections 203a and 203b where each portion or section includes a plurality of fiber layers. An outlet port 205 provides an exit from the media dispensing device 200 to dispense the fluid from the media dispensing device 200. In certain implementations, the outlet port 205 can include a wick (not shown). As shown in FIG. 2, the fluid reservoir 201 and the gradient density reservoir 203 are positioned within the media dispensing device 200 in a vertical arrangement. However, the instant disclosure also contemplates other arrangements, such as a vertical, a horizontal or an angular orientation with respect to the fluid reservoir. FIG. 3 illustrates an exemplary embodiment of a horizontal configuration. In FIG. 3, the media dispensing device 300 includes a fluid gradient reservoir 303 and corresponding portions or sections 303a, 303b positioned with a horizontal orientation with respect to a fluid reservoir 301.

Referring back to FIG. 2, in operation, for example, the fluid migrates from the fluid reservoir 201 into the gradient density reservoir 203 and is ultimately dispensed through the outlet port 205. As the fluid is dispersed through the outlet port 205, air can be drawn into the media dispensing device 200. This air then migrates to the fluid reservoir 201, causing a static pressure to build within the media dispensing device 200. The static pressure enables the fluid to flow into and through the gradient density reservoir 203.

In certain embodiments, the fluid reservoir 201 can be separated from the gradient density reservoir 203 by a wall positioned within the media dispensing device 200. This wall can include a hole, pore, matrix or pores, or other similar opening (not shown) which permits the free flow of the fluid from the fluid reservoir 201 into the gradient density reservoir 203. In other embodiments, the fluid reservoir 201 may be separated from the gradient density reservoir 203 by a fluid-permeable membrane.

In certain implementations, the gradient density reservoir 203 may include a plurality of fiber layers. In some embodiments, the plurality of fiber layers include a first portion of fiber layers 203a having a first density (referred to herein as a "low density layer") and a second portion of fiber layers 203b having a second density (referred to herein as a "high density layer"). In one embodiment, the high density layer may have a density ranging from about 0.11 g/cm$^3$ to about 0.25 g/cm$^3$. In another embodiment, the high density layer may have a density ranging from about 0.12 g/cm$^3$ to about 0.24 g/cm$^3$. In another embodiment, the high density layer may have a density ranging from about 0.13 g/cm$^3$ to about 0.23 g/cm$^3$. In yet another embodiment, the high density layer may have a density ranging from about 0.14 g/cm$^3$ to about 0.22 g/cm$^3$. In some embodiments, the high density layer may have a density ranging from about 0.15 g/cm$^3$ to about 0.21 g/cm$^3$. In some embodiments, the high density layer may have a density ranging from about 0.16 g/cm$^3$ to about 0.19 g/cm$^3$. In some embodiments, the high density layer may have a density ranging from about 0.16 g/cm$^3$ to about 0.18 g/cm$^3$. In one embodiment, the density of the high density layer is greater than the density of the low density layer. In one embodiment, the low density layer may have a density ranging from about 0.01 g/cm$^3$ to about 0.10 g/cm$^3$. In one embodiment, the low density layer may have a density ranging from about 0.02 g/cm$^3$ to about 0.09 g/cm$^3$. In one embodiment, the low density layer may have a density ranging from about 0.03 g/cm$^3$ to about 0.08 g/cm$^3$. In one embodiment, the low density layer may have a density ranging from about 0.04 g/cm$^3$ to about 0.07 g/cm$^3$. In one embodiment, the low density layer may have a density ranging from about 0.05 g/cm$^3$ to about 0.06 g/cm$^3$.

In certain implementations, there can be overlap in the densities of the high and low density zones. For example, the high density zone can have a density ranging from about 0.05 g/cm$^3$ to about 0.25 g/cm$^3$, and the low density zone can have a density ranging from about 0.01 g/cm$^3$ to about 0.15 g/cm$^3$.

In one embodiment, the high density layer and the low density layer each have a substantially uniform density. In another embodiment, the high density layer and the low density layer each have a graduated density. In another embodiment, the high density layer has a substantially uniform density and the low density layer has a graduated density. In yet another embodiment, the high density layer has a graduated density and the low density layer has a substantially uniform density. In one embodiment, the gradient density reservoir has a density variation from a first end to a second end ranging from about 0.05 g/cm$^3$ to about 0.2 g/cm$^3$. In another embodiment, the density variation ranges from about 0.06 g/cm$^3$ to about 0.19 g/cm$^3$. In another embodiment, the density variation ranges from about 0.07 g/cm$^3$ to about 0.18 g/cm$^3$. In another embodiment, the density variation ranges from about 0.08 g/cm$^3$ to about 0.17 g/cm$^3$. In another embodiment, the density variation ranges from about 0.09 g/cm$^3$ to about 0.16 g/cm$^3$. In another embodiment, the density variation ranges from about 0.10 g/cm$^3$ to about 0.15 g/cm$^3$. In another embodiment, the density variation ranges from about 0.11 g/cm$^3$ to about 0.14 g/cm$^3$. In another embodiment, the density variation ranges from about 0.12 g/cm$^3$ to about 0.13 g/cm$^3$.

The gradient density reservoir can further include a height ratio. The "height ratio" is defined of a value of a geometric property of the high density layer divided by the same geometric property value of the low density layer. The geometric property can include a height, thickness, length, etc. For example, the height ratio can be a calculation of the height of the high density layer divided by the height of the low density layer. In one embodiment, this height ratio can range from about 1 to about 50. In another embodiment, the height ratio can range from about 5 to about 45. In another embodiment, the height ratio can range from about 10 to about 40. In another embodiment, the height ratio can range from about 15 to about 35. In another embodiment, the height ratio can range from about 20 to about 30.

As stated herein, the gradient density reservoir is comprised of a plurality of fiber layers. The fiber layers can include fibers made from a polymeric material or combination of polymeric materials. In one embodiment, the porous fiber matrix includes bicomponent fibers. In another embodiment, the porous fiber matrix includes bicomponent fibers and mono-component fibers.

In some embodiments, the fibers can include one or more of a polyester and a co-polyester. In certain embodiments, the polyester or co-polyester can include one or more of polyethylene terephthalate (PET), polybutylene terephthalate (PBT), polytrimethylene terephthalate (PTT) and poly (lactic acid) (PLA). In one embodiment, the fiber layers may include fibers made from PLA. Bicomponent fibers that may be employed in the practice of this invention include, but are not limited to fibers constructed from the following pairs of polymers: polypropylene/polyethylene terephthalate (PET), polyethylene (PE)/PET, polyethylene/polypropylene, polypropylene/Nylon-6, Nylon-6/PET, copolyester/PET, copolyester/Nylon-6, copolyester/Nylon-6,6, poly-4-methyl-1-pentene/PET, poly-4-methyl-1-pentene/Nylon-6, poly-4-methyl-1-pentene/Nylon-6,6, PET/polyethylene naphthalate (PEN), Nylon-6,6/poly-1,4-cyclohexanedimethy-1 (PCT), polypropylene/polybutylene terephthalate (PBT), Nylon-6/ co-polyamide, polyester/polyester and polyurethane/acetal.

The plurality of fiber layers of the gradient density reservoir can include individual layers of carded non-woven webs. In other embodiments, the individual layers include a woven material. In another embodiment, the individual layers include a staple fiber. In another embodiment, the individual layers include a continuous fiber. In yet another embodiment, the fibers of the individual layers have a fiber mass in the range of from about 1 to about 20 dtex. In one embodiment, the fibers of the individual layers have a fiber diameter ranging from about 5 microns to about 35 microns. In other embodiments, the fibers can have a fiber diameter ranging from about 5 microns to 10 microns, from about 10 microns to 15 microns, from about 15 microns to 20 microns, from about 20 microns to 25 microns, from about 25 microns to 30 microns, from about 30 microns to 35 microns, and other similar ranges of diameters.

The density of the high density layer and low density layer can be achieved by manipulating various physical factors of the fibers used in the fiber layers. Manipulating physical factors, such as fiber density, fiber diameter, fiber mass, and fiber surface, varies the density of a fiber layer or layers. The density of a fiber layer can be manipulated by, for example, compressing fiber layers, resulting in more fibers per cubic centimeter over less compressed fiber layers. In other embodiments, the fiber density can be manipulated by increasing the number of fibers in the fiber layer, employing fibers of greater diameter and/or fiber mass, or any combination thereof. Other methods of manipulating fiber density in a fiber layer are also contemplated and such methods would be apparent to those of skill in the art in view of this disclosure.

Manipulating fiber density, at the same time, manipulates the capillarity of the fiber matrix. Generally the higher the fiber matrix density means the higher capillarity.

Alternatively, the fibers used in the fiber layers can be classified according to fiber energy. In certain implementations, the fibers can have a fiber energy range of about 29 dyne/cm to about 50 dyne/cm. In some examples, the fibers can be treated with a finish or lubricant, resulting in the fibers being fully wettable (i.e., having a contact angle=0).

In certain embodiments, the density of the first portion of fiber layers can be greater than the density of the second portion of fiber layers.

In certain examples, such as those shown in FIGS. 5A, 5B, and 5C described below, there can be a portion of the gradient density reservoir 203 where the first portion of the fiber layer 203a transitions into the second portion of the fiber layer 203b, thereby defining a gradual transition from the first density (the low density layer) to the second density (the high density layer). As such, the single-piece fiber matrix can eliminate a defined interface between the first portion 203a and the second portion 203b.

As noted above, as the fluid is dispensed via the outlet port 205, air is introduced into the media dispensing device 200. The uptake of air into the media dispensing device 200 creates a static pressure in the media dispensing device 200, thereby enabling fluid to migrate from the fluid reservoir 201 to the gradient reservoir 203. The static pressure drives fluid from the fluid reservoir 201 through the gradient capillarity reservoir 203 to the wick. The capillarity effect of the gradient density reservoir 203 via the fiber layers in the first portion of fiber layers 203a and the second portion of fiber layers 203b increases the wicking action of the fluid to more fully utilize the fluid in the media dispensing device 200.

In certain implementations, the density gradient is generally perpendicular to the fiber orientation of the fiber layers in the gradient reservoir 203. In another embodiment, the capillary gradient is in line with the fiber orientation of the fiber layers in the gradient reservoir 203. It is understood that the density gradient directly relates to a capillary force. As used herein, "capillary force" relates the wicking motion of the gradient reservoir 203, and is defined as the ability of a fluid to flow in through the gradient reservoir 203 without the assistance of external forces, such as gravity.

In one embodiment, the fiber layers in the high density layer and the fiber layers in the low density layer are substantially cohesive. As used herein, "cohesive" means that there are substantially no gaps creating between the fiber layers in the high density layer and the fiber layers in the low density layers. Further, the interface between the high density layer and the lower density layer is substantially cohesive. In one embodiment, the fiber layers of the high density layer and/or the low density layer can be adhered to form a cohesive interface. In another embodiment, the fiber layers are adhered by an adhesive. In one embodiment, the fiber layers are adhered by compressing the fiber layers together.

Figure 5:
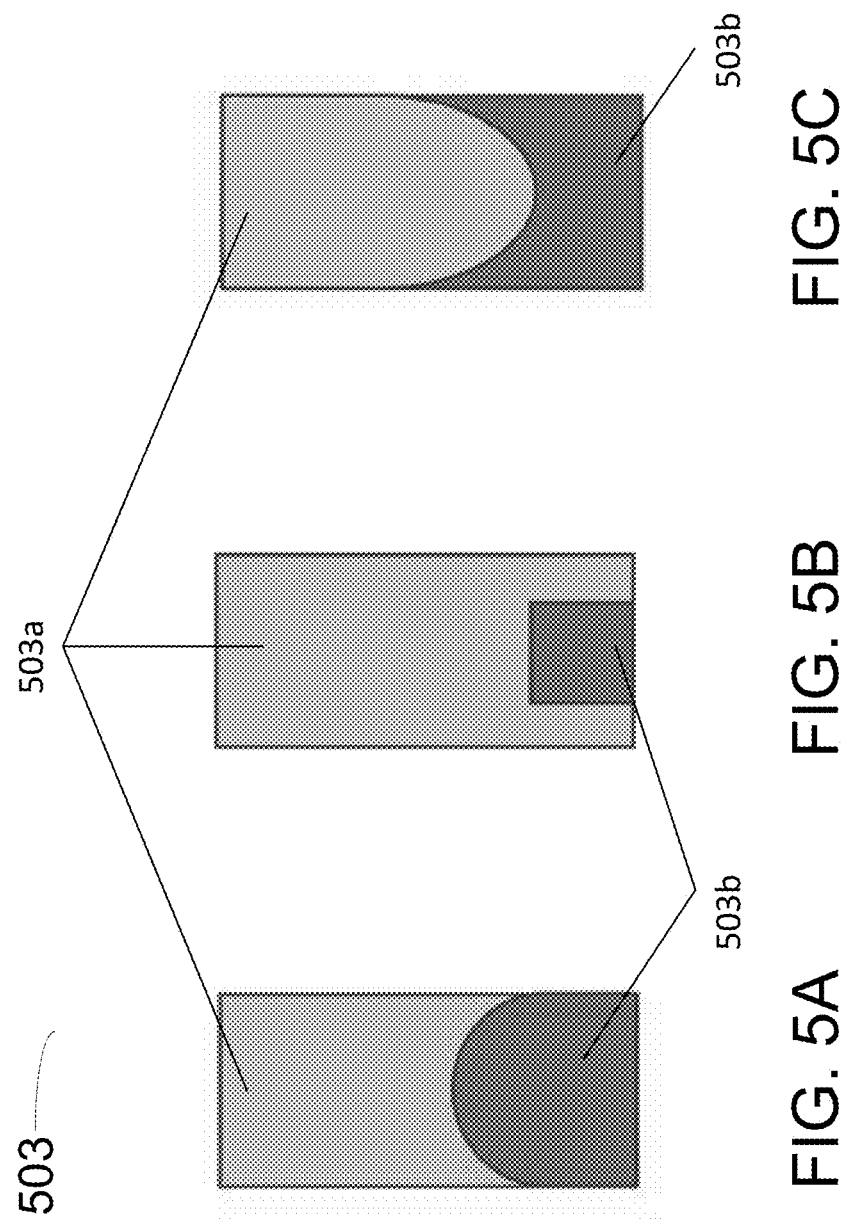
FIG. 5A illustrates examples of reservoirs with gradient density according to an embodiment.
FIG. 5B illustrates examples of reservoirs with gradient density according to an embodiment.
FIG. 5C illustrates examples of reservoirs with gradient density according to an embodiment.

FIGS. 5A, 5B and 5C illustrate alternative configurations for a gradient reservoir 503. In FIG. 5A, the first portion of fiber layers 503a and the second portion of fiber layers 503b have a crescent-shaped interface where the second portion of fiber layers 503b has a thicker middle portion that tapers to generally thin points on the sides. FIG. 5B also features a crescent-shaped interface; however, in this embodiment, the first portion of fiber layers 503a is thicker in the middle and tapers to generally thin points on the sides. In FIG. 5C, the second portion of fiber layers 503b is generally square or rectangular and is surrounded on two sides by the second portion of fiber layers 503a. Other embodiments are also contemplated in view of this disclosure.

Examples

Figure 4:
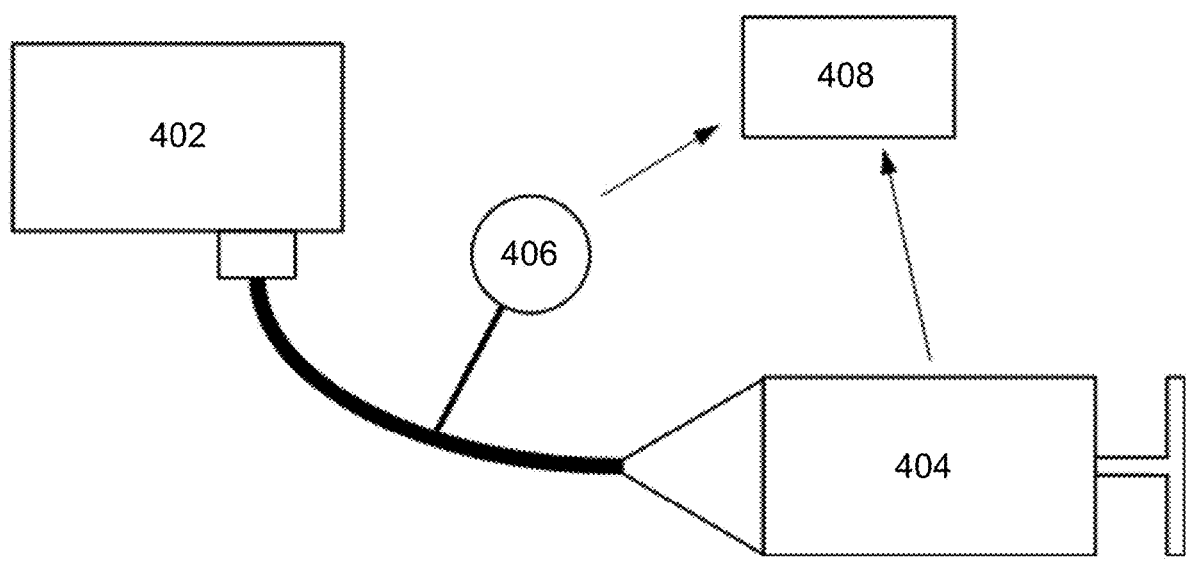
FIG. 4 illustrates a testing apparatus setup for testing internal fluid reservoirs in accordance with one or more embodiments described herein.

Samples were tested on an internal fluid reservoir extraction stand (for example, an ink reservoir extraction stand). FIG. 4 illustrates a sample extraction test apparatus 400. A media dispensing device 402 can be connected via tubing to a pressure source, such as syringe pump 404. The syringe pump 404 can be configured to create a negative pressure in the tubing, there facilitating extraction of a fluid from the media dispensing device 402. A pressure transducer 406 can be attached to the tubing between the media dispensing device 402 and the syringe pump 404. The pressure transducer 406 can be configured to measure a pressure in the tubing throughout the test. Pressure reading values along with additional information such as pressure flow rate or time for a constant flow rate can be sent to a data recording device 408 for recordation. This information can be later accessed and analyzed to determine additional data related to the test. For example, a plot of pressure versus fluid extraction can be determined based upon the recorded information.

In certain implementations, a specific time and extraction rate can be used to simulate a specific test case. For example, the samples can tested using an extraction rate set at 0.30 cc/min, and the static pressure can be measured after, for example, the first 90 seconds.

Phase 1 Results:

A two component system having high density media ("HDM") and low density media ("LDM") reservoirs was produced using a combination of both low and high density fibers that would mimic the design of the integrated density gradient reservoir. As a result, the system pressures were lower and the extraction efficiencies were higher than the control commercial product. Extraction results are summarized in TABLE 4 below:

TABLE 4

| Sample | Length Ratio | Low Density | High Density | extraction efficiency, % | Dynamic Press Inches of Water | Static Press Inches of Water |
|---|---|---|---|---|---|---|
| | | | | Average of n = 4 | | |
| A | 1.24 | 0.06 | 0.11 | 80.97 | 4.03 | 1.75 |
| B | 1.94 | 0.09 | 0.11 | 81.86 | 4.39 | 2.16 |
| C | 1.94 | 0.06 | 0.14 | 81.12 | 3.99 | 1.73 |
| D | 1.24 | 0.09 | 0.14 | 85.21 | 3.58 | 2.04 |
| E | 1.59 | 0.075 | 0.125 | 83.95 | 3.57 | 1.87 |
| Current Product | 1.54 | 0.09 | 0.11 | 69.95 | 5.85 | 3.45 |

Note:
Length Ratio is equal to the Low density width (or height in cartridge) divided by the High density width.

Phase 2 Results:

TABLE 5 below provides a summary of the overall density of the combined (HDM plus LDM) reservoirs of Phase 1. The Phase 2 reservoirs were produced with an overall density of 0.09 g/cm³.

TABLE 5

| Sample | Width mm | Thickness mm | Length mm | Weight g | Density g/cc |
|---|---|---|---|---|---|
| A | 31.8 | 8.2 | 39.6 | 0.85 | 0.08 |
| B | 31.8 | 8.2 | 39.6 | 0.80 | 0.08 |
| C | 31.8 | 8.2 | 39.6 | 1.00 | 0.10 |
| D | 31.8 | 8.2 | 39.6 | 0.90 | 0.09 |
| E | 31.8 | 8.2 | 39.6 | 1.16 | 0.11 |
| Current product | 31.8 | 8.2 | 39.6 | 1.01 | 0.10 |

Two samples were made in a top-to-bottom (A) and side-to-side (B) configuration as discussed herein. TABLE 6 illustrates the data for these two samples:

TABLE 6

| Sample | Extraction Eff % | Dynamic Press Inches of Water | Static Press Inches of Water |
|---|---|---|---|
| A | 86.84 | 3.42 | 1.99 |
| B | 84.83 | 4.19 | 2.02 |

The sample A and B show high extraction (release) efficiency.

Sample Embodiments

Figure 6:
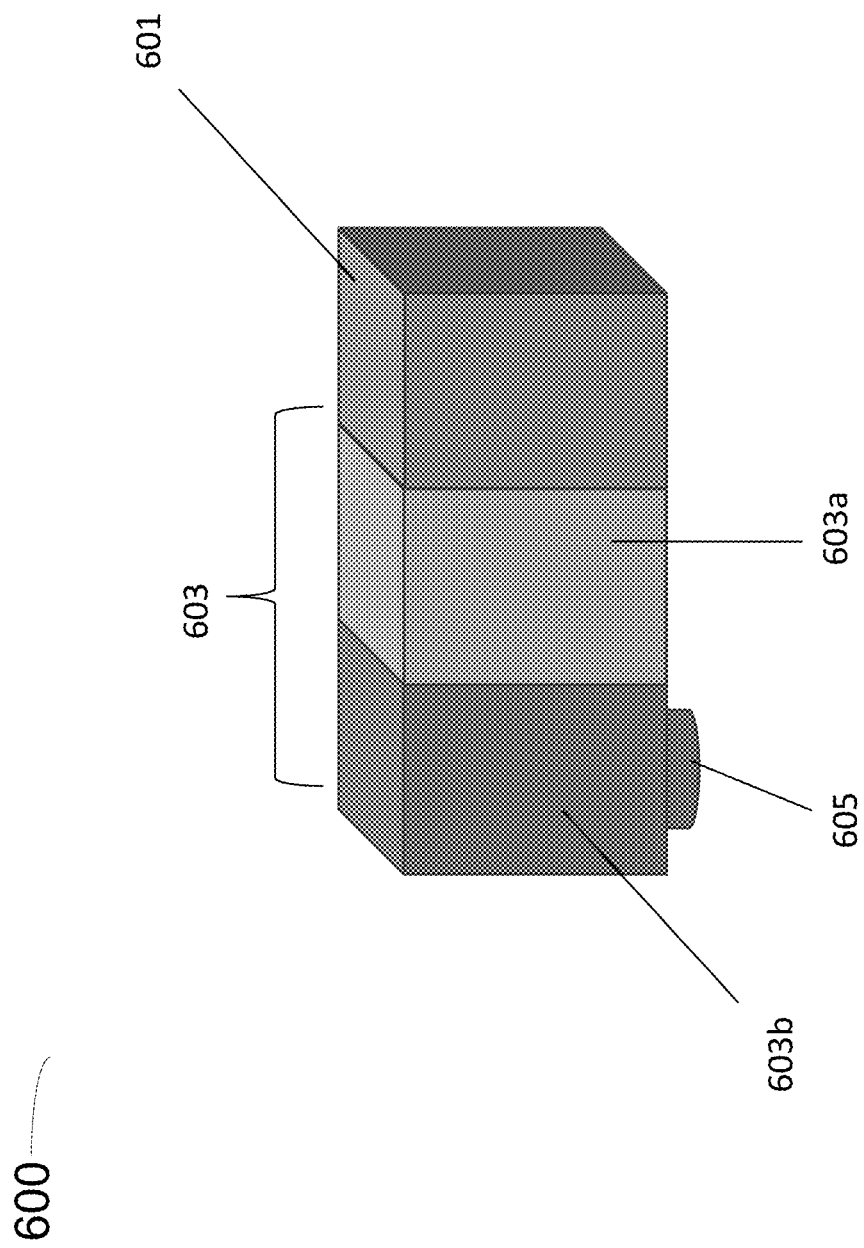
FIG. 6 illustrates an ink cartridge in accordance with one or more embodiments described herein.
Figure 7:
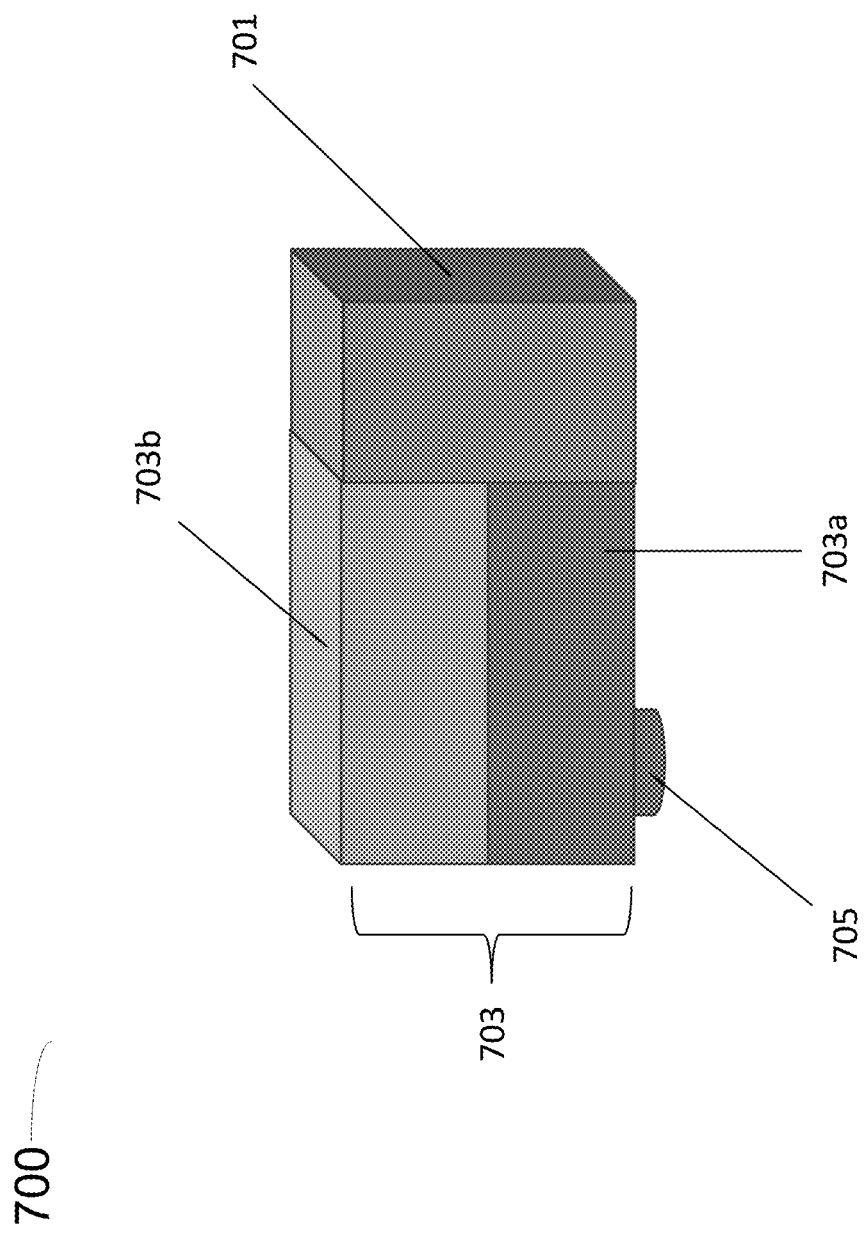
FIG. 7 illustrates an ink cartridge in accordance with one or more embodiments described herein.

As noted above, a specific example of a media dispensing device including a single-piece reservoir including a gradient density reservoir. In one embodiment, the ink cartridge includes an ink reservoir containing free, i.e., liquid, ink used in a printing process. The ink reservoir is in fluid communication with the gradient density reservoir. FIG. 6 illustrates an exemplary embodiment of an ink cartridge 600. In FIG. 6, the ink cartridge 600 includes an ink reservoir 601 and a gradient density reservoir 603 in fluid communication with the ink reservoir 600. The gradient density reservoir 603 includes two portions or sections 603a and 1003b where each portion or section includes a plurality of fiber layers. An outlet port 605 provides an exit from the ink cartridge 600 to dispense ink from the ink cartridge 600. The outlet port 605 may include a wick (not shown). In the embodiment of FIG. 6, the ink reservoir 601 and the gradient density reservoir 603 are positioned within the ink cartridge 600 in a vertical arrangement. In contrast, FIG. 7 illustrates an alternate embodiment of a horizontal configuration. In FIG. 7, the ink cartridge 700 includes an ink gradient reservoir 703 and corresponding portions or sections 703a, 703b positioned with a horizontal orientation with respect to the ink reservoir 701.

Turning back to FIG. 6, in operation, for example, liquid ink migrates from the ink reservoir 601 into the gradient density reservoir 603 and is ultimately dispensed through the outlet port 605. As ink is dispersed through the outlet port 605, air is drawn into the ink cartridge 600. This air then migrates to the ink reservoir 601, causing a static pressure to build within the ink cartridge 600. The static pressure enables ink to flow into and through the gradient density reservoir 603.

In some embodiments, the ink reservoir 601 can be separated from the gradient density reservoir 603 by a wall positioned within the ink cartridge 600. This wall can include a hole or pore (not shown) which permits the free flow of ink from the ink reservoir 601 into the gradient density reservoir 603. In other embodiments, the ink reservoir 601 may be separated from the gradient density reservoir 603 by an ink-permeable membrane.

As further shown in FIG. 6, the gradient density reservoir 603 may include a plurality of fiber layers. In some embodiments, the plurality of fiber layers include a first portion of fiber layers 603a having a first density and a second portion of fiber layers 603b having a second density. In an alternate embodiment, the high density layer and the low density layer each have a substantially uniform density. In another embodiment, the high density layer and the low density layer each have a graduated density. In another embodiment, the high density layer has a substantially uniform density and the low density layer has a graduated density. In yet another embodiment, the high density layer has a graduated density and the low density layer has a substantially uniform density. In one embodiment, the density of the first portion of fiber layers is greater than the density of the second portion of fiber layers.

Referring again to FIG. 6, as ink is dispensed via the outlet port 605, air is introduced into the ink cartridge 600. This air migrates through the gradient reservoir 603 to the ink reservoir 601. The uptake of air into the ink cartridge 600 creates a static pressure in the ink cartridge 600, thereby enabling ink to migrate from the ink reservoir 601 to the gradient reservoir 603. The static pressure drives ink from the ink reservoir 601 through the gradient density reservoir 603 to the wick. The density effect of the gradient density reservoir 603 via the fiber layers in the first portion of fiber layers 603a and the second portion of fiber layers 603b increase the wicking action of the ink to more fully utilize substantially all of the ink in the ink cartridge 600. In one embodiment, the density gradient is generally perpendicular to the fiber orientation of the fiber layers in the gradient reservoir 603. In another embodiment, the capillary gradient is in line with the fiber orientation of the fiber layers in the gradient reservoir 603. It is understood that the density gradient directly relates to a capillary force. As used herein, "capillary force" relates the wicking motion of the gradient reservoir 603, and is defined as the ability of ink to flow in through the gradient reservoir 603 without the assistance of external forces, such as gravity.

The integral porous fluid deposition and dispensing media's density or capillarity could be adjusted for different fluid formulations, such as fluid viscosities, surface tensions, solid contents and chemical compositions for the best deposition and dispensing performance. Generally, lower viscosity fluid requires a higher density media and a higher viscosity fluid pity media. But other factors also affect the media selection, such as appearance, external compression or suction forces, fluid flow properties and vaporization speed. In certain implementations, the media of present invention can be compatible with fluid from 1 cps to 20,000 cps.

Additionally, the media as described herein can be manufactured using existing manufacturing techniques. For examples, the processes and techniques as described in U.S. Pat. No. 7,888,275, the content of which is incorporated herein by reference in its entirety, can be used to manufacture and/or produce the media as described herein.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by 1/10 of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the claims include equivalents to the recited values, e.g., variations in the numerical quantity of such values that can occur, but would be recognized to be equivalents by a person skilled in the art.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. An integral porous fiber matrix comprising:
    a plurality of density regions, including a high density region and a low density region, wherein each of the plurality of density regions has a different fiber density; and
    a plurality of diameter regions, wherein each of the plurality of diameter regions has a different fiber diameter;
    wherein the integral porous fiber matrix is configured to hold and release a quantity of one or more liquid compositions;
    wherein a ratio of the fiber density of the high density region to the fiber density of the low density region is from 1.1:1 to 1.5:1;
    wherein the fiber diameter ranges from 2 dtex to 15 dtex; and
    wherein the integral porous fiber matrix comprises a single unit, such that the plurality of density regions are not separable.

2. The integral porous fiber matrix of claim 1, wherein the matrix is integrated into a cushioned disk, and wherein the one or more liquid compositions are cosmetic compositions.

3. The integral porous fiber matrix of claim 1, further comprising bicomponent fibers.

4. An integral porous fluid depository and delivery media comprising an integral porous fiber matrix, the matrix comprising:
    a plurality of density regions, including a high density region and a low density region, wherein each of the plurality of density regions has a different fiber density; and
    a plurality of diameter regions, wherein each of the plurality of diameter regions has a different fiber diameter;
    wherein the integral porous fiber matrix is configured to hold and release a quantity of one or more liquid compositions;
    wherein a ratio of the fiber density of the high density region to the fiber density of the low density region is from 1.1:1 to 1.5:1;
    wherein the fiber diameter ranges from 2 dtex to 15 dtex; and
    wherein the matrix comprises a single unit, such that the plurality of density regions are not separable.

5. The integral porous fluid depository and delivery media of claim 4, wherein a change in density of the plurality of density regions is gradual.

6. The integral porous fluid depository and delivery media of claim 4, wherein the matrix is integrated into a cushioned disk.

7. The integral porous fluid depository and delivery media of claim 4, further comprising bicomponent fibers.

8. The integral porous fluid depository and delivery media of claim 7, wherein the bicomponent fibers comprise at least one of polypropylene/polyethylene terephthalate (PET), polyethylene (PE)/PET, polyethylene/polypropylene, polypropylene/Nylon-6, Nylon-6/PET, copolyester/PET, copolyester/Nylon-6, copolyester/Nylon-6,6, poly-4-methyl-1-pentene/PET, poly-4-methyl-1-pentene/Nylon-6, poly-4-methyl-1-pentene/Nylon-6,6, PET/polyethylene naphthalate (PEN), Nylon-6,6/poly-1,4-cyclohexanedimethy-1 (PCT), polypropylene/polybutylene terephthalate (PBT), Nylon-6/co-polyamide, polyester/polyester and polyurethane/acetal.

9. The integral porous fluid depository and delivery media of claim 4, wherein the one or more liquid compositions comprise at least one of a writing instrument ink, an inkjet ink, a cosmetic composition, a foundation, a perfume, a sunscreen, an oil, a gel, and a liquid therapeutic agent.

10. The integral porous fluid depository and delivery media of claim 4, wherein the fiber density includes a varying range comprising at least one of 0.005 g/cm$^3$ to 0.2 g/cm$^3$, from 0.01 g/cm$^3$ to 0.18 g/cm$^3$, and from 0.02 g/cm$^3$ to 0.15 g/cm$^3$.

11. The integral porous fluid depository and delivery media of claim 4, wherein different density regions comprise different capillary forces.

12. The integral porous fluid depository and delivery media of claim 4, wherein gradient density regions comprise gradient capillary forces.

13. A fluid application device including at least one integral porous fluid depository and a delivery media including an integral porous fiber matrix, the matrix comprising:
  a plurality of density regions, including a high density region and a low density region, wherein each of the plurality of density regions has a different fiber density; and
  a plurality of diameter regions, wherein each of the plurality of diameter regions has a different fiber diameter;
  wherein the integral porous fiber matrix is configured to hold and release a quantity of one or more liquid compositions;
  wherein a ratio of the fiber density of the high density region to the fiber density of the low density region is from 1.1:1 to 1.5:1;
  wherein the fiber diameter ranges from 2 dtex to 15 dtex; and
  wherein the matrix comprises a single unit, such that the plurality of density regions are not separable.

14. The fluid application device of claim 13, wherein the device comprises at least one of a cushion compact foundation device, a perfume application device, a makeup device, an ink jet printer cartridge, a writing instrument, and a medical device.

* * * * *